United States Patent
Caputi et al.

(10) Patent No.: US 10,322,039 B2
(45) Date of Patent: Jun. 18, 2019

(54) ABSORBENT ELEMENT FOR DISPOSABLE ABSORBENT ARTICLES HAVING AN INTEGRATED ACQUISITION LAYER

(71) Applicant: The Procter & Gamble Company, Cincinnati, OH (US)

(72) Inventors: Mariangela Caputi, Pescara (IT); Norbert Matthais Stelzer, Idstein (DE); Michele Mazzeo, Francavilla Al Mare (IT); Carola Elke Beatrice Krippner, Waldems (DE); Gerard A. Viens, Wyoming, OH (US); Christopher Philip Bewick-Sonntag, Cincinnati, OH (US); Remo Bellucci, Blue Ash, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 557 days.

(21) Appl. No.: 14/729,103

(22) Filed: Jun. 3, 2015

(65) Prior Publication Data

US 2015/0342802 A1 Dec. 3, 2015

(30) Foreign Application Priority Data

Jun. 3, 2014 (EP) .................................... 14170912

(51) Int. Cl.
*A61F 13/537* (2006.01)
*A61F 13/51* (2006.01)
(Continued)

(52) U.S. Cl.
CPC .... *A61F 13/5376* (2013.01); *A61F 13/15642* (2013.01); *A61F 13/15658* (2013.01);
(Continued)

(58) Field of Classification Search
CPC ............ A61F 13/51; A61F 2013/51004; A61F 2013/51038; A61F 2013/5104;
(Continued)

(56) References Cited

U.S. PATENT DOCUMENTS 4,100,324 A * 7/1978 Anderson ............ C11D 17/049
156/167
4,723,954 A 2/1988 Pieniak
(Continued)

FOREIGN PATENT DOCUMENTS

DE 20118532 U1 2/2002
WO WO-9311725 A1 * 6/1993 ....... A61F 13/47218
WO WO-2014186570 A1 * 11/2014 ........... A61L 15/225

OTHER PUBLICATIONS

Tayebi et al., "Effect of Delustering Agent on Physical and Mechanical Properties of Nylon 6," 2011, Asian Journal of Chemistry, vol. 23, No. 1, pp. 398-402. (Year: 2011).*
(Continued)

*Primary Examiner* — Cheryl Juska
(74) *Attorney, Agent, or Firm* — Andrew J. Hagerty; Brian M. Bolam (57) ABSTRACT

The present invention relates to a layers layered absorbent element for use in a disposable absorbent article comprising a top layer and a bottom layer. The top layer is a fibrous nonwoven layer having a basis weight of from 20 to 100 gsm, a thickness from 0.25 to 5 mm, is formed with fibers having an average length from 26 to 200 mm and it has a fixed height saturation at 5 cm above 40%. The bottom layer is in direct contact with the top layer and comprises superabsorbent polymer (SAP) and cellulosic fibers. A plurality of fibers protruding from the bottom layer penetrate into the top layer.

13 Claims, 1 Drawing Sheet

(51) Int. Cl.
*A61F 13/53* (2006.01)
*A61F 13/539* (2006.01)
*A61F 13/15* (2006.01)

(52) U.S. Cl.
CPC .............. *A61F 13/51* (2013.01); *A61F 13/53* (2013.01); *A61F 13/539* (2013.01); *A61F 2013/51019* (2013.01); *A61F 2013/530481* (2013.01); *A61F 2013/530868* (2013.01)

(58) Field of Classification Search
CPC .......... A61F 13/53; A61F 2013/530131; A61F 2013/53024; A61F 2013/530481; A61F 2013/530868; A61F 13/539; A61F 13/5376
See application file for complete search history.

(56) References Cited

U.S. PATENT DOCUMENTS

| | | | | |
|---|---|---|---|---|
| 4,950,264 | A * | 8/1990 | Osborn, III | A61F 13/15203 604/385.08 |
| 5,447,677 | A * | 9/1995 | Griffoul | A61F 13/15658 264/113 |
| 5,607,414 | A * | 3/1997 | Richards | A61F 13/15203 604/358 |
| 5,858,515 | A * | 1/1999 | Stokes | A44B 18/0011 156/167 |
| 5,972,487 | A * | 10/1999 | Duenk | A61F 13/534 428/212 |
| 6,127,594 | A | 10/2000 | Rosseland | |
| 6,235,966 | B1 * | 5/2001 | Magnusson | A61F 13/15642 604/365 |
| 6,383,960 | B1 * | 5/2002 | Everett | A61F 13/535 442/317 |
| 6,416,697 | B1 * | 7/2002 | Venturino | A61F 13/15658 264/113 |
| 6,461,086 | B1 * | 10/2002 | Milanowski | B65G 53/14 406/173 |
| 6,528,439 | B1 * | 3/2003 | Stokes | A61F 13/62 264/477 |
| 6,533,978 | B1 * | 3/2003 | Wisneski | A61F 13/15658 264/113 |
| 6,533,989 | B1 * | 3/2003 | Wisneski | D04H 1/4374 264/510 |
| 7,081,559 | B2 * | 7/2006 | Fujikawa | A61F 13/539 442/271 |
| 7,642,207 | B2 * | 1/2010 | Boehmer | B32B 5/28 442/382 |
| 8,628,456 | B2 * | 1/2014 | Stelzer | B31F 7/00 493/340 |
| 8,771,471 | B2 * | 7/2014 | Singh | A61F 13/15617 162/218 |
| 9,138,360 | B1 * | 9/2015 | Febo | A61F 13/534 |
| 10,034,800 | B2 * | 7/2018 | Febo | A61F 13/534 |
| 2002/0013560 | A1 * | 1/2002 | Erspamer | A61F 13/15203 604/381 |
| 2003/0012919 | A1 * | 1/2003 | Dutkiewicz | A61F 13/535 428/76 |
| 2004/0116882 | A1 * | 6/2004 | Erspamer | A61F 13/8405 604/359 |
| 2005/0167874 | A1 * | 8/2005 | Larsson | A61F 13/15626 264/122 |
| 2007/0077428 | A1 * | 4/2007 | Hamed | D06M 13/00 428/393 |
| 2007/0152365 | A1 * | 7/2007 | Dutkiewicz | A61F 13/535 264/113 |
| 2014/0005623 | A1 * | 1/2014 | Wirtz | A61F 13/534 604/366 |
| 2014/0087618 | A1 * | 3/2014 | Newkirk | D01D 5/08 442/335 |
| 2014/0343523 | A1 * | 11/2014 | Viens | A61L 15/225 604/370 |
| 2015/0342789 | A1 * | 12/2015 | Caputi | A61F 13/15707 156/62.2 |
| 2015/0366728 | A1 * | 12/2015 | Febo | A61F 13/534 604/365 |
| 2016/0136012 | A1 * | 5/2016 | Peri | A61F 13/537 604/372 |
| 2017/0095380 | A1 * | 4/2017 | Wirtz | A61F 13/534 |
| 2017/0119587 | A1 * | 5/2017 | Bewick-Sonntag | A61F 13/15203 |
| 2017/0119597 | A1 * | 5/2017 | Bewick-Sonntag | A61F 13/15203 |

OTHER PUBLICATIONS

Barker, R.H., "Additives in Fibers and Fabrics," Environmental Health Perspectives, Jun. 1975, vol. 11, pp. 41-45. (Year: 1975).*
PCT International Search Report, dated Sep. 29, 2016, 50 pages.

* cited by examiner

ABSORBENT ELEMENT FOR DISPOSABLE ABSORBENT ARTICLES HAVING AN INTEGRATED ACQUISITION LAYER

FIELD OF THE INVENTION

The present invention relates to an absorbent element which can be used in disposable absorbent articles such as sanitary napkins, panty liners, baby diapers, adult incontinence articles and sweat pads. According to the present invention the absorbent element is formed by a top layer performing the function of an acquisition and optionally of distribution layer and a bottom layer performing primarily the function of a storage layer wherein, at the interface between the acquisition layer and the storage layer the fibers of the storage layer interpenetrate the fibers of the acquisition/distribution layer.

The absorbent element of the present invention is designed to allow an improved integration between top and bottom layers, i.e. between acquisition/distribution and storage layers resulting in improved liquid handling when compared with prior art solutions.

The absorbent element of the invention can be used as an absorbent core in disposable absorbent articles sandwiching it between a topsheet and a backsheet. Optionally other layers and absorbent elements can be present in the absorbent article as it will be described in more detail below.

BACKGROUND OF THE INVENTION

Absorbent elements for disposable absorbent articles are commonly formed by different individual material layers which are superimposed, wherein each material layer is designed to provide specific properties. A typical structure for an absorbent element includes an acquisition layer and a storage layer, other layers can also be present such as a distribution layer, a tissue layer, a layer to provide resiliency to the products (bunching resistance), or a layer to provide a better visual impression etc. as known in the art.

The acquisition layer is typically placed on top of the body facing surface of the storage layer and has the function of rapidly acquire the fluids excreted from the body and to transfer them rapidly away from the body into the storage layer, and also to keep the storage layer separate enough from the skin so to avoid that body fluids can rewet the skin during the usage of the absorbent articles. In some cases the acquisition layer has also, as secondary function, the function of distributing the fluid on a larger surface area so to provide a more efficient usage of the surface of the storage layer. In other cases this distribution function can be performed by a portion of the storage layer or by a separate layer having this specific function. This distribution layer can be placed for example below the storage layer on the surface of the storage layer which is opposite to the body facing one (garment facing surface).

In some technical documents typically relating to Feminine care articles the acquisition layer is also called "secondary topsheet". In the present application, the term "acquisition layer" is intended to be equivalent and to include also "secondary topsheets".

Each of the mentioned layers can be formed by one or more sub layers, for example the storage layers can be formed by 2 or more sub layers having the same or different functions and/or chemical composition. Also the acquisition layer can independently be formed by more sub layers, having different functions and/or chemical composition. For example, in case the acquisition layer also performs a fluid distribution function, the portion of the acquisition layer closer to the body facing surface of the absorbent element can act transferring the fluids away from the body and the portion closer to the bottom layer can act distributing the fluid along a broader surface before migrating into the storage layer.

A problem associated with using these multilayer structures as absorbent elements in absorbent articles is that fluid transfer from one layer to the other can be non optimal when the layers are separate due to the discontinuity in fluid communication. Traditionally this has been solved by using adhesives such as latexes or hot melt glues at the interface of the layers to bond the layers together, however these adhesive materials can in turn impede the fluid transfer.

In order to solve this problem "unitary" absorbent elements have been developed. The word "unitary" refers to a single structure, which, despite potential internal variations of physical and/or chemical characteristics, is provided such that it cannot be separated into individual layers without destroying the structure or damaging the layers at their interface. Absorbent structures made from a number of layers, which are joined to each other by macroscopic mechanical or adhesive means are not considered unitary since they are formed from individual layers that, albeit sometimes with difficulty, can be separated from each other again.

In other words, similarly to conventional multilayer structures, "unitary" absorbent elements are formed by several layers which can have distinct properties and/or compositions from one to the other. But, while in a "non unitary" absorbent element there is a definite boundary from one layer to the other, in a "unitary" absorbent element the various layers are somehow intermixed at the boundary region so that, instead of a definite boundary between layer it will be possible to identify a region where the different layers transition one into the other. This unitary structure is built forming the various sub-layers one on top of the other in a continuous manner, for example using air laid or wet laid deposition. Typically there is no adhesive used between the sub-layers of the of a unitary material, as this is not necessary due to the unitary construction and the combining being conducted on the layers, however in some cases adhesives and/or binders can be present although typically in a lower amount than in multilayer materials formed by separate layers.

Unitary absorbent elements have been disclosed previously e.g. in WO03/090656A1 from Procter & Gamble, US2002/007169A1 from Weyerhaeuser and WO00/74620A1 from Buckeye.

In unitary absorbent elements the fluid communication between the layers is improved, but the performance of these absorbent elements can still be further improved, especially as concerns the performance of the acquisition layer and the fluid transfer properties at the interface between acquisition and storage layer.

The "unitary" absorbent elements described in the prior art are essentially of two types. A first type does not include the fluid acquisition layer in the unitary structure. When these absorbent elements are used in a disposable absorbent article an additional acquisition layer, which is typically required, needs to be applied as a separate layer as in conventional absorbent structures. As a consequence the fluid communication between the acquisition layer and the storage layer suffers of the same drawbacks mentioned above for the non unitary structures.

A second type of unitary absorbent elements described in the prior art includes an integrated acquisition layer which is formed by the same process and with the same technique of the remaining part of the absorbent element.

For example US2002/007169 from Weyerhauser describes unitary absorbent elements produced using a wet laid process, where the various layers are formed one on top of the other, and where also the acquisition layer is formed with a wet laid process.

In WO00/74620A1 from BKI absorbent elements are described which are formed using an air laid process wherein three different layers are deposited in sequence on a tissue carrier and wherein the last layer to be deposited on top is a synthetic PET fibers air laid layer which is supposed to work as an acquisition layer.

These absorbent elements of the prior art can still be improved because the technologies (such as wet or air laid process) which allow the production of desirable storage layer materials, are not always suitable to manufacture acquisition layers having the desired properties.

In particular air and wet laid technologies have inherent limitations in the length of the fibers which can be deposited. In particular the fibers effectively usable in air/wet laid processed are in relatively short, in the range of 8-20 mm. Moreover in materials resulting from air and wet laid methods the fibers tend to be all oriented in the x,y plane, and due to the nature of the air and wet laying methods wherein all the various layers are deposited one on top of the other before further processing of the material, the fibers for the acquisition layer cannot be rearranged or processed independently.

In some cases it is desirable to produce acquisition layers with longer fibers (from 26 to 200 mm long). As known to the skilled person, long fibers can impart peculiar properties to nonwovens especially as concerns fluid handling. Long fibers can generate longer connected pores leading to increased wicking capability as it can be measured using vertical wicking height tests.

Additionally long fibers in a separately made material can be rearranged along the z axis if desired (using consolidation techniques such as hydroentangling or needlepunching) thus allowing to obtain a wide range of finely tunable fluid handling properties. For examples fibers oriented in all direction in a 3D structure can provide tunable resilience and porosity properties to the acquisition layer. Z-direction fibres an also create fluid handling channels that quickly bring the fluid away from the surface.

There is therefore a need to use long fibers in acquisition layers. This is currently possible only by using separate nonwoven layers for example hydroentangled, air trough bonded, needlepunched, spunbond, carded resin bonded and meltblown nonwovens. However the use of a separate nonwoven layer faces the problems (mentioned above) concerning that fluid transfer from one layer to the other is non optimal due to the discontinuity in fluid communication.

The absorbent elements of the present invention have the advantage of using a selected non woven material which can be manufactured separately as acquisition layer. This non woven material can therefore be tailored and tuned to provide the desired fluid transfer properties by forming it and consolidating it using conventional techniques such as e.g. carding, needlepunching or hydroentangling. At the same time an improved integration between acquisition layer and storage layer is achieved due to fiber interpenetration (described in detail below). This allows using less adhesives and binders such as latexes at the interface between acquisition and storage layer (or even no adhesives and latex binders) with the result of maximising the fluid communications between the layers and without compromising on the acquisition properties of the layer.

SUMMARY OF THE INVENTION

The present invention relates to a layered absorbent element for use in a disposable absorbent article, said absorbent element comprising:
i) a top layer having a first surface and a second surface which is a fibrous nonwoven layer having a basis weight of from about 20 gsm (grams per square meter) to about 100 gsm, and a thickness from about 0.25 mm (millimeters) to about 5 mm,
   the nonwoven layer is formed with fibers having an average length from about 26 mm to about 200 mm,
   the nonwoven layer has a fixed height saturation at 5 cm above 40%;
and
ii) a bottom layer having a first surface and a second surface, the first surface of the bottom layer is in direct contact with the second surface of the top layer, the bottom layer comprises superabsorbent polymer (SAP) and fibers, including cellulosic fibers,
   and wherein a plurality of fibers protruding from the first surface of said bottom layer penetrate into the top layer through its second surface.

DETAILED DESCRIPTION OF THE INVENTION

All percentages are to be considered as weight percentages unless otherwise specified.

The unit "gsm" is intended as grams per square meter.

The term "absorbent article" is used herein in a broad sense including any article able to receive and/or absorb and/or contain and/or retain body fluids/bodily exudates such as menses, vaginal secretions, urine and faeces. Exemplary absorbent articles in the context of the present invention are disposable hygiene absorbent articles such as feminine hygiene absorbent articles such as sanitary napkins and pantyliners, baby diapers, adult incontinence pads and diapers. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical absorbent articles according to the present invention are sanitary napkins, panty liners, absorbent pads for low, moderate or high incontinence, baby diapers or pants, as well as diapers and pants for adult incontinence. Absorbent articles according to the present invention include a fluid pervious topsheet, a backsheet, which may be fluid impervious and/or may be water vapour and/or gas pervious, and an absorbent core comprised there between. The term "absorbent core" in the present invention indicates the combination of all layers and materials which are sandwiched between the topsheet and the backsheet (excluding topsheet and backsheet). The absorbent element according to the present invention is used as a component of the absorbent core. The absorbent element of the invention may constitute the entire absorbent core of the absorbent article or the absorbent core of the absorbent article can comprise other layers and/or other absorbent elements.

Absorbent articles according to the present invention include various types of structures, from a simple structure where the absorbent element of the invention is sandwiched between a topsheet and a backsheet to more complex multi layer structures where additional layers and/or absorbent elements are present. In a typical multilayer construction, the absorbent article is made by a topsheet and a backsheet which sandwich an absorbent element according to the present invention and an additional acquisition layer positioned between the topsheet and the absorbent element.

In all cases, when describing the article and the absorbent structure of the present invention, it is considered that the article and the absorbent structure are in a flattened configuration where the plane of the article is the x,y plane and the z axis is perpendicular to said plane.

The term "treated pulp" is equivalent to "softener treated pulp" and to "debonder treated pulp" refers to fluff pulp treated with debonding agents which reduce the strength of hydrogen bonding between cellulose molecules.

The topsheet of the absorbent hygienic article is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), polymeric materials such as apertured formed thermoplastic films, apertured plastic films, and hydroformed thermoplastic films, porous foams, reticulated foams, reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like. Topsheets may be formed by one or more layers made of the materials mentioned above, where one layer forms the outer surface of the absorbent article and one or more other layers are positioned immediately below it. The layer forming the outer surface of the article is typically a nonwoven layer or a formed film and it can be treated to be hydrophilic using surfactants or other means known to the person skilled in the art.

The backsheet can be impervious to liquids (e.g., menses and/or urine) and can be preferably manufactured from a thin plastic film, although other flexible materials may also be used such as nonwovens. As used herein, the term "flexible" refers to materials which are compliant and will readily conform to the general shape and contours of the human body. The backsheet can prevent the exudates absorbed and contained in the absorbent core from wetting articles which contact the absorbent article such as bedsheets, pants, pajamas and undergarments. The backsheet can also be vapor permeable ("breathable"), while remaining fluid impermeable. In an embodiment, a microporous polyethylene or polyethylene polypropylene film can be used as backsheet. The backsheet can be formed by one or more layers and may comprise a woven or nonwoven material, polymeric films such as thermoplastic films of polyethylene or polypropylene, or composite materials such as a film-coated nonwoven material.

The backsheet can comprise panty fastening means applied on its surface, particularly the surface facing outside the absorbent article in order to allow the article to stay in place when worn between the user's crotch and panties. Such panty fastening means can be for example a layer of adhesive or mechanical means such as Velcro® or combination thereof. When an adhesive is present, typically a release paper is also present in order to protect the adhesive before use.

The backsheet and the topsheet can be positioned respectively adjacent the garment surface and the body surface of the absorbent core. The absorbent core can be joined with the topsheet, the backsheet, or both in any manner as is known by attachment means such as those well known in the art. Embodiments of the present invention are envisioned wherein portions of the entire absorbent core are unattached to the topsheet, the backsheet, or both.

Absorbent articles of the present invention may comprise side flaps. Side flaps (known to the skilled person also as "wings" or "side panels") are disclosed in the literature and are available in the marketplace. Generally, side flaps extend laterally from a central portion of the absorbent article and are intended to be folded around the edges of the wearer's panties in the crotch region. Thus, the flaps are disposed between the edges of the wearer's panties in the crotch region and the wearer's thighs. Commonly, the flaps are provided with an attachment means for affixing the flaps to the underside of the wearer's panties. In most cases the attachment means is similar or equal to the panty fastening means of the backsheet e.g. a layer of adhesive.

The flaps serve at least two purposes. First, the flaps prevent exudates which otherwise would soil the edges of the wearer's panties from doing so. Second, the flaps help stabilize the napkin from shifting out of place, especially when the flaps are affixed to the underside of the panties.

Sanitary napkins having flaps of the various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,271, entitled "Sanitary Napkin", which issued to Clark on Apr. 2, 1957.

Side flaps can be separate elements which are attached to the sides of the main body of the absorbent article along its perimeter. Alternatively they can be formed by an extension of elements forming the main body of the article such as the topsheet, the backsheet or both. In some cases also other layers forming the absorbent article such as the absorbent core, or a secondary topsheet can extend to the side flaps.

The present invention relates to a layered absorbent element having a surface extending in the x,y plane and a thickness extending in the z direction. The absorbent element of the present invention has a first surface which, when in use, is intended to face the body of the user (body facing surface) and an opposing second surface which during use faces toward the opposite direction (garment facing surface).

Typically the absorbent element is rectangularly shaped, for ease of manufacturing. However, it may be differently shaped, for example there is frequently a wearer preference for an absorbent element which is narrower at the center than at the ends, to comfortably accommodate the legs, and obviate or minimize occurrences of bunching or wadding of the element. Oval shaped absorbent elements have also been proposed (e.g. WO2005/084596A1).

The absorbent element according to the present invention comprises a top layer and a bottom layer, typically the absorbent element of the present invention consists of a top and a bottom layer in the sense that no other layers are present (even if, as it will be detailed below the top and bottom layers can independently include sub-layers). The top layer has the primary function of acquiring the fluids, optionally distributing said fluids over a larger surface area and then quickly transferring them to the bottom layer, the bottom layer has the primary function to act as storage layer i.e. store the absorbent fluids and prevent them from rewetting the user and optionally distributing them over a larger surface area so to ensure optimal utilization of the absorbent material.

The top layer has a first surface and a second surface wherein the first surface coincides with the body facing surface of the absorbent element, and the second surface is oriented toward the garment of the user.

The bottom layer comprises a first surface and a second surface. The first surface of the bottom layer is oriented towards and is in direct contact with said second surface of said top layer, while the second surface of the bottom layer is the garment facing surface of the absorbent element.

The top layer of an absorbent element according to the present invention is a fibrous nonwoven layer comprising fibers having an average length from 26 to 200 mm (or from 30 to 150, or from 30 to 100 mm). In some embodiments the average fiber size in dtex can be selected so to be in the range from 0.5 to 15 dtex (or from 1 to 5 dtex or from 1 to 4 dtex). The average fiber length is measured according to ASTM method D5103-07 and the average size in dtex according to the ASTM method D1577-07. The nonwoven layer forming the top layer has a basis weight of from 20 to 100 gsm (or from 25 to 90 gsm) and a thickness (measured according to the method described herein) from 0.2 to 5 mm (or from 0.25 mm to 4 mm, or from 0.3 mm to 3 mm, or from 0.4 mm to 2 mm).

Said nonwoven is selected in order to have a fixed height saturation at 5 cm (FHS5, measured according to the method described herein) above 40%. Nonwoven materials having this parameter in the desired range typically have good acquisition properties.

Nonwoven layers having the desired fixed height saturation value can be easily provided by a person skilled in the art for example by selecting the nonwoven layer among needlepunched, hydroentangled, air through bonded, spunbonded, carded resin bonded, and melt blown non woven materials. Additional parameters that a skilled person can vary in order to tune the FHS5 are the diameter of the fibers, their cross section, their resiliency and their blend ratios.

FHS5 is dependent from the pore size or, in other words, by the size of the spaces between the fibers. Larger spaces provide a lowered FHS5 value. Fibers having a larger diameter or cross section will form layers having larger spaces between the fibers and consequently lower FHS5. As mentioned, in some embodiments a suitable range of average fiber diameter in dtex is from 0.5 to 15 dtex. A preferred range is from 1 to 5 dtex and an even more preferred one from 1 to 4 dtex.

The compaction of a layer will in general reduce the void spaces, but the resiliency of the fibers has an effect on how much compaction will in effect reduce the void spaces.

Finally fibers of different diameter can be blended in order to obtain intermediate values for FHS5.

Hydroentangled and needlepunched nonwovens are in some cases preferred because these consolidation technologies allow to obtain materials having a good z-direction compression resistance, and good capillarity even at low basis weight (thus allowing to manufacture thinner and lower cost absorbent elements).

In some embodiments the nonwoven layer forming the top layer comprises from 5 to 70 wt % or from 10 to 60 wt % of multicomponent binder fibers, and it is thermally bonded by them. The remaining fibers can be selected from natural, regenerated and synthetic fibers. In order to improved wettability it is preferred that at least 90% wt of the fibers (or in some embodiment 100% wt) are hydrophilic or are hydrophilically treated (e.g. with a surfactant) so to exhibit hydrophilic properties. In some embodiments also the multicomponent binder fibers can be treated so to exhibit hydrophilic properties.

Example of fibers suitable for use in the top layer in addition to the multicomponent binder fibers are synthetic or regenerated fibers selected from PET, polyethylene, polypropylene, nylon, rayon, polylactic acid and mixture thereof. Natural fibers may also be present such cellulosic fibers, for example cotton and/or pulp fibers.

As mentioned the top layer may comprise multicomponent binder fibers. Multicomponent binder fibers are fibers commonly used as binders and are known to the skilled person. Typically they comprise at least a bonding component and a structural component. The bonding component is a thermoplastic material which has a softening point which is lower than that of the structural component. Thermal bonding is achieved by heating the material at a temperature above the softening point of the bonding component and below the softening temperature of the structural component.

In some embodiments the multicomponent binder fibers are bicomponent binder fibers. Bicomponent binder fibers can be formed for example by polyethylene and polypropylene, polyethylene/polyethylene terephthalate, metallocene PP with PET core, and can have any configuration known in the art such as for example core-sheath, star, fiber eccentric, fiber concentric, side by side, and mixture thereof.

The thickness of the top layer in the absorbent element of the present invention is between 0.25 mm and 5 mm, or from 0.25 mm and 4 mm, or from 0.3 mm and 3 mm, or from 0.4 mm and 2 mm. Top layers having a very low thickness, below 0.25 mm, are not preferred because a top layer which is too thin might not be effective in preventing rewet. A very high thickness, above 5 mm, is also not preferred because it adds unnecessary bulk to the absorbent article. In general for menstrual articles a thickness between 0.25 and 1 mm is preferred while for urine management articles a thicker top layer is preferred in a range from 0.5 mm to 2 mm.

A particularly suitable material for the top layer is a hydroentangled fibrous structure having a basis weight between 35 grams per square meter (gsm) and 65 gsm, a machine direction (MD) bending stiffness (measured according to EDANA test method no. WSP 090.5 (Bending Length Stiffness)) of 0.2 mN·cm to 7 mN·cm, and a rewet value (measured according to EDANA test method no. WSP 070.7 (Repeated Liquid Strike-Through Time) of 0.2 g to 7.0 g. This material comprises 30% to 60%, by weight, of cellulosic fibers, 5% to 30%, by weight, of non-cellulosic fibers, and 30% to 55%, by weight, of polyolefin-based multicomponent binder fibers.

The Bottom Layer

The bottom layer of an absorbent element according to the present invention has the primary purpose to absorb and retain body fluids and can have any of the typical structures and compositions of absorbent cores and storage layers for disposable absorbent articles as known in the art.

The bottom layer can be any fibrous absorbent member which is generally compressible, conformable, non-irritating to the wearer's skin, and capable of absorbing and retaining body fluids. For "fibrous" it is meant that it comprises fibers. In some embodiments fibers represent at least 15% of the total weight of the bottom layer.

The absorbent element can comprise a wide variety of liquid-absorbent materials commonly used in disposable absorbent articles. Non-limiting examples of liquid-absorbent materials suitable for use in the bottom layer of the absorbent element include comminuted wood pulp which is generally referred to as airfelt or pulp; creped cellulose wadding; chemically stiffened, modified, or cross-linked cellulose fibers, cotton fibers; meltblown polymers including co-form; synthetic fibers including crimped polyester fibers; capillary channel fibers; absorbent foams; absorbent sponges; synthetic staple fibers and superabsorbent polymers (SAP). Some embodiments may use, as pulp, finer fibered eucalyptus pulp, this is particularly useful in the portion of bottom layer which faces the top layer because due to its finer fibers may generate a higher and deeper penetration of the fibers from the bottom layer into the top layer.

Multicomponent binder fibers such as those described for the top layer can also be present in the bottom layer. If present in the bottom layer multicomponent fibers will represent typically 2 to 20% by weight of the total weight of the bottom layer and the bottom layer is thermally bonded by them. In some embodiment the multicomponent binder fibers are bicomponent binder fibers. Bicomponent binder fibers can be formed for example by polyethylene and polypropylene, polyethylene/polyethylene terephthalate, metallocene PP with PET core, and can have any configuration known in the art such as for example core-sheath, star, fiber eccentric, fiber concentric, side by side, and mixture thereof.

The configuration and construction of the bottom layer may include one or more sub layers.

In some embodiments SAP represents from 5 to 75% by weight of the total weight of the bottom layer or from 5 to 65%, or from 15 to 50%. Other optional constituents of the bottom layer of the absorbent element according to the present invention are binders (such as latex) or glues.

Optionally latex, as a dust control means, can be applied onto the second surface of the absorbent element in an amount of 0.1%-2% by weight of the bottom layer.

In a preferred embodiment of the present invention the bottom layer comprises superabsorbent polymers (SAP) and cellulosic fibers (such as cellulose, rayon, viscose etc.) and the combination of these two component represents at least 80% wt of the total weight of the bottom layer.

In case one or more sub-layers are present for the bottom layer each of the mentioned optional components can be present in one or more of the sub-layers, and can be present at different concentrations in each of the sub-layers.

Superabsorbent polymers (SAP) are known in the art and are defined herein as polymeric materials that can absorb at least 10 times their weight of an aqueous 0.9% saline solution as measured using the Centrifuge Retention Capacity test (EDANA WSP 241.2-05). Any superabsorbent polymer can be used in the present invention. Examples of superabsorbent polymers are absorbent gelling materials (AGM), and superabsorbent foam materials.

Absorbent gelling materials (AGM), are typically used in finely dispersed form, e.g. typically in particulate or fiberized form, in order to improve their absorption and retention characteristics. AGM typically comprises water insoluble, water swellable, hydrogel forming crosslinked absorbent polymers which are capable of absorbing large quantities of liquids and of retaining such absorbed liquids under moderate pressure. Absorbent gelling materials can be incorporated in absorbent articles, typically in the core structure, in different ways; for example, absorbent gelling materials in particulate form can be dispersed among the fibres of one or more of the fibrous layers comprised in the core, or rather localized in a more concentrated arrangement between fibrous layers so that one or more of the layers making up the core comprise a reduced amount of fibrous materials and/or are essentially made of SAP.

Other examples of SAP according to the present invention are porous or foamed superabsorbents such as those described in WO2010118272A1, WO2013180832A1 and WO2013180937A1 usable both as layers and in particulate form.

Absorbent articles according to the present invention may comprise any of the SAPs mentioned above or a mixture thereof.

In some embodiments the bottom layer can be provided for example as a fibrous stratified layer structure with at 2 or more sub-layers, for example 3 sub-layers or 4 sub-layers or 5 sub-layers.

When the bottom layer has a stratified structure such stratified structure can form a so called "unitary" structure. Unitary structures in absorbent elements for absorbent articles are known in the art and described for example in are described in in WO03/090656A1 from Procter & Gamble, US2002/007169A1 from Weyerhaeuser and WO00/74620A1 from Buckeye as mentioned above in the "Background of the invention" section. These documents describe absorbent cores having a unitary structure. In the present invention the same type of unitary structure can be used to form the bottom layer of the absorbent element of the present invention and it can be obtained by simply forming the "bottom layer" of the absorbent element of the invention on the second surface of its "top layer" in the same way as the absorbent cores of the cited documents are formed, for example using air or wet laid equipment, as it will described more in detail further on.

In some embodiments at least three sub-layers are present. The at least three sub-layers of the bottom layer comprise a first outermost sub-layer oriented toward the wearer-facing surface of the absorbent element and in direct contact and fluid communication with the garment facing surface of the top layer, a second outermost sub-layer, which forms the garment-facing surface of the absorbent element and at least one inner sub-layer, which is sandwiched between the first and the second sub-layers.

In some embodiments the first sub-layer comprises softener treated fluff pulp and bicomponent binder fibers, the second sub-layer comprises treated fluff pulp, and optionally bicomponent binder fibers, and at least one of the inner sub-layers comprises untreated fluff pulp, and optionally bicomponent binder fibers.

Treated pulp in the first sub-layer, due to the reduced effect of hydrogen bonding, has a more open structure than untreated pulp, such a sub-layer cooperates with the top layer in driving the fluid away from the body.

In an alternative embodiment the first sub-layer comprises untreated pulp and SAP (and optionally bicomponent binder fibers), this is desirable when the primary objective is acquisition speed.

In a further alternative embodiment the second sub-layer comprises untreated pulp and SAP (and optionally bicomponent binder fibers).

Optionally the second layer also comprises optionally comprises a surface binder, preferably latex, as a dust control means, which is applied onto the garment-facing surface of the absorbent element in an amount of 0.1%-2% by weight of the bottom layer.

Each and all sub-layers can comprise SAP. In some cases only some of the sub-layers comprise SAP. In these embodiments SAP will be comprised at least in one or more of the inner sub-layers.

For example SAP can be comprised only in one or more of the inner sub-layers, or alternatively it can be comprised also one or both of the first (i.e. in usage closer to the body) and the second sub-layer (i.e. in usage further away from the body). A design where SAP is closer to the body can be advantageous because SAP in a more proximal position to the body will absorb and retain more body fluids than cellulosic fibers and thus reduce rewet. The alternative design wherein SAP is absent from the first sub-layer closer to the body and present in the second layer can be advantageous to improve acquisition speed and store the fluid away from the body.

In all the mentioned embodiments it is possible include optionally an embossment on the second surface of the bottom layer. Embossments might be beneficial to the wet integrity of the core, and to increase its density while reducing its stiffness.

In all embodiments where SAP is present in the first sub-layer it is preferred that the open structure of the top layer does not have too large pores, at least in its portion along the z axis immediately facing the first surface of the bottom layer, this because SAP, especially in case SAP is AGM, can have small particle size and if the top layer has too large pores some of the AGM can be lost from the absorbent element.

The use of unitary structure for the bottom layer allows for the use of less glue so that in some embodiments the absorbent element of the present invention is free of binder material, except for the bi-component fibers and the optional surface binder on its garment-facing surface.

An essential feature of the absorbent element present invention is that a plurality of fibers of the bottom layer protrude from the first surface the bottom layer and penetrate into said top layer through its second surface.

This structure allows a good interconnection and fluid communication between the top and the bottom layer. In particular it is believed that the fibers from the bottom layer while penetrating the second surface of the top layer generate a bond between the layers which is also due to a certain degree of fibers entanglement between the fibers of the top layer and the fibers of the bottom layer. In addition the cellulosic fibers originating in the bottom layer and penetrating the top layer play a role in that they help to drive the fluid away from the top layer by capillary action.

In some embodiments the top layer comprises multicomponent binder fibers and at least some of said plurality of fibers protruding from the bottom layer and penetrating into the top layer are bonded to multicomponent binder fibers which are part of the top layer. In this case the bonding and the connection between the two layers are further improved because the binder fiber maintain the two layers in closer contact even when the absorbent element is in use and is subject to stretches and movements.

The absorbent elements according to the various embodiments of the present invention allow to use a reduced amount additional adhesives and binders (such as in particular adhesives such as hot melt glues and/or latexes) between the top and bottom layers, which is desirable both from the economic and environmental standpoint and because glues adhesives and binders, as known, can have a negative effect of the capacity of the absorbent element to efficiently transport fluids at the interface between top and bottom layer.

In some embodiments no latex and or hot melt glue binders are present at the interface between top and bottom layer.

One way of achieving the interpenetrated structure of the present invention is to manufacture the absorbent element on an wet laid or airlaid line wherein the non woven material forming the top layer is used as a forming screen and wherein the components for making the bottom layer are deposited onto the top layer using conventional airlaid or wet laid techniques.

In some cases the nonwoven of the top layer is a pre-formed nonwoven. For pre-formed it is intended that the nonwoven layer is manufactured and sourced separately and then integrated with the rest of the absorbent element on the airlaid or wetlaid line.

In an airlaid process individual fibers are conveyed using an air flux to forming heads on an airlaid web forming machine. Typically the loose fibers are kept in motion within the forming head (via rotation, agitation or other means) to ensure they do not entangle with each other, and are then pulled by a vacuum onto a perforated surface on which the fibers are deposited.

In a traditional air laid process the deposition occurs on a light nonwoven material layer or a tissue layer used as a substrate. Such light substrate, typically, does not impact the fluid acquisition and distribution properties of the airlaid material but merely acts as a substrate which helps maintaining the integrity of the air laid web when it is removed from the perforated surface for subsequent processing.

In the present case the nonwoven forming the top layer is used as the substrate on which the fibers are deposited in the air laid line. A specific advantage of using this process for the present invention is that in the case of the present invention the use of a light nonwoven or tissue layer is not necessary because the nonwoven material of the top layer acting as a substrate for the airlaid formation provides the required integrity to the resulting web, so that the resulting absorbent element does not require the use of an additional layer such as the tissue or light non woven layer which provides no advantages in terms of fluid handling.

The interpenetrated structure is formed because the air flow containing fibers for forming the bottom layer passes through the top layer used as a forming screen, the air flow pressure pushes the fibers onto the long pores present in the second surface of the top layer so that at the end of the process a significant number of fibers from the bottom layer extends into the pores of the second surface of the top layer.

When the deposition of the air laid bottom layer is complete the resulting material is typically compressed to compact it (e.g. via calendering). In case multicomponent binder fibers are present in the top layer the material can be thermally treated at a temperature above the softening temperature of a bonding component of the multicomponent binder fibers of the top layer and below the softening point of a structural component in the multicomponent binder fibers of the top layer so that the binder fibers from the top layer can bind fibers from the bottom layer. In case also the bottom layer comprises multicomponent binder fibers some of its binder fibers can penetrate the second surface of the top layer and bond to fibers from the top layer. In this case the treatment temperature should be chosen so to be above the softening temperature of a bonding component of the multicomponent binder fibers of both layers layer and below the softening point of a structural component in the multicomponent binder fibers of both layers.

Optionally the resulting material is treated with additional binders on the second surface of the bottom layer (such as a latex binder) to avoid dusting, the compression and thermal treatment steps can also optionally include the formation of an embossment on the second surface of the bottom layer and/or on the first surface of the top layer.

The resulting sheet of material can then be cut if necessary in the appropriate size and used as absorbent element within the absorbent core of an absorbent article.

As known, when a multilayer structure is desired for the bottom layer (i.e. a structure having sub-layers of different composition) the bottom layer can be formed on an air laid machinery having several forming heads (in general one for each layer even if it could be imagined that one forming head could form two or more non adjacent layers) and wherein each forming head lays down a specific combination of materials in a given set of conditions. In this process a first forming head forms a first air laid layer, then a second forming forms a second air laid layer on top of the first layer. The process goes on until the desired series of sub-layers is obtained. In the present invention the bottom layer can be formed by one layer or, two sub-layers, or three sub-layers, or four sub-layers or five sub-layers, or by even more than five sub-layers. In the case where more forming heads are present it is possible to conduct also compression steps between the passage from one forming head to the other.

Typically the deposition of an air laid layer or sub-layer the composition of the materials (fibers/agm, etc.) deposited by each forming head is constant, however it is also possible to envision embodiments of the present invention wherein the composition of the materials (fibers/agm, etc.) deposited by each forming head varies with time. This allows generating a continuous variation of composition and properties of the material along its z axis in a single layer or sub-layer.

Exemplary multilayer structures for the bottom layer are any airlaid unitary absorbent cores such as those described in the cited documents WO03/090656A1 from Procter & Gamble, and WO00/74620A1 from Buckeye. The same composition and processes described in the cited prior art can be employed to build the bottom layer in the present invention with the difference that, as mentioned above, in producing the absorbent elements of the present invention on an air laid line it will not be necessary to use a light nonwoven or tissue layer to provide integrity to the material because this function is performed by the nonwoven layer of the top layer which used as forming screen.

Naturally also other manufacturing techniques within the capacity of the skilled person can be used to manufacture the invention. For example a similar interpenetration of fibers could be obtained also using the top layer as a forming screen in a wet laid deposition process such as that as described in US2002/007169 from Weyerhauser.

In a typical embodiment, the absorbent elements of the present invention can be incorporated as absorbent structures into absorbent articles, for example as absorbent cores or as part of their absorbent cores.

As mentioned above an absorbent article according to the present invention can be simply formed by a topsheet and a backsheet sandwiching the absorbent substructure of the invention which acts as absorbent core.

However additional layers and/or absorbent structures can be present as apparent to the skilled person.

The absorbent core can optionally comprise for example an additional distribution layer positioned between the absorbent element and the backsheet or an additional "secondary topsheet" or "acquisition layer".

As mentioned above, the absorbent element of the present invention contains a top layer which performs the function of a secondary topsheet or acquisition layer. Therefore absorbent articles according to the present invention may not include an additional separate layer for this purpose so that the topsheet can be in direct contact with the absorbent element.

In some embodiments it may be desirable that the absorbent article comprises an additional acquisition layer positioned between the topsheet and the absorbent element. In this case the additional acquisition layer and the top layer of the absorbent element are preferably in direct face to face contact and the basis weight of the additional acquisition layer will be in general much lower than the typical basis weight of an acquisition in a similar absorbent article because the top layer of the absorbent element cooperates in the acquisition capacity of the absorbent article. For example in the present invention it is desirable for an additional acquisition layer, if present, to have a basis weight of 10 to 80 grams per square meter, more preferred for it to have a basis weight of 10-50 grams per square meter, and most preferred for it to have a basis weight of between 10 and 40 grams per square meter.

In case an additional acquisition layer is present it is preferred that its surface in the xy plan is at least coextensive as the corresponding surface of the absorbent element of the invention. In some further preferred embodiments the surface of the additional acquisition layer is larger than the surface of the absorbent element so that the additional acquisition layer extends further than the absorbent element in substantially all directions. In this case the additional acquisition layer can also perform the function of providing a more pleasing aesthetical aspect to the absorbent article e.g. a dogbone shaped acquisition layer can be provided which is superimposed to a rectangular absorbent element, so that the user can perceive or visualize trough the topsheet the more pleasant dogbone shape thus masking the more basic rectangular shape of the absorbent element.

Examples of materials and structures for additional acquisition layers which are usable in the present invention are those described in WO2012040315A1.

Further additional layers may be present in the absorbent article as known in the art, distribution layers, dusting layers, impermeabilizing patches, etc.

In an alternative embodiment of the invention the absorbent element comprises a top layer comprising a nonwoven, comprising some z-direction fiber orientation (e.g. due to hydroentangling, needlepunching, or other solid state treatment) and a bottom layer comprising fibers and SAP. Some of the fibers from the bottom layer extend into the top layer to create a second level of z-direction fiber orientation.

Also in an alternative embodiment the absorbent element comprises a top layer comprising a nonwoven comprising synthetic fibers and a first type of cellulosic fibers (e.g. rayon) and a bottom layer comprising synthetic fibers, SAP, and a second type of cellulosic fibers (e.g. pulp). A plurality of cellulosic fibers of the second type protruding from the first surface of the bottom layer penetrate into the top layer through its second surface.

Example

An exemplary absorbent element according to the invention can be made by following the procedure described herein:

Provide a hydroentangled fibrous nonwoven layer having a basis weight of 55 gsm, with smooth surface and a homogeneous blend of (1) about 40% viscose rayon fibers (1.7 dtex, 38 mm staple length), (2) about 40% bicomponent fibers formed from polypropylene (PP) and polyethylene (PE) (1.7 dtex, 40 mm length, PE sheath 50% by weight and PP core 50% by weight), which includes about 1.0% titanium dioxide (TiO2), and (3) about 20% polyethylene terephthalate (PET) (40 mm staple length).

Use this nonwoven layer as forming screen in an air laid equipment having three forming heads.

The forming heads contain the following distribution of materials:

Forming head 1: 20% wt bicomponent binder fibers (2 dtex, 50% core PP, 50% sheath PE from Woongjin) 80% wt softener treated cellulose pulp from Georgia Pacific.

Forming head 2: 30% wt AGM (superabsorbent cross linked polyacrylate available from Nippon Shokubai) 70% wt untreated cellulose pulp from Weyerhaeuser.

Forming head 3: 20% wt AGM (superabsorbent cross linked polyacrylate available from Nippon Shokubai) 78% untreated cellulose pulp from Weyerhaeuser, 2% wt Latex binder (from Wacker Airflex 192).

Activate the air laid equipment and lay down directly on the nonwoven surface a 50 gsm layer from forming head 1, then a 50 gsm layer from forming head 2 and finally a 50 gsm layer from forming head 3.

Remove the material from the air laid line and compress it with a calendering roll and finally dry the material at a temperature of 131° C. until completely dry.

Test Methods

Unless otherwise specified, all tests described herein were conducted on samples conditioned at a temperature of 73° F.±4° F. (about 23° C.±2.2° C.) and a relative humidity of 50%±4% for 2 hours prior to the test.

Thickness

The thickness of a layer of the absorbent element structure according to the present invention, as well as of a combinations of layers, for example of an entire absorbent element structure, can be measured with any available method known to the skilled person under the selected confining pressure of 0.25±0.01 psi. For example, the INDA standard test method WSP 120.1 (05) can be used, wherein for the "Thickness testing gage" described under section 5.1, the "applied force", section 5.1.e, is set at 0.25±0.01 psi, and the "Readability", section 5.1.f, has to be 0.01 mm.

Fixed Height Saturation (FHS) at 5 cm Test Method

This test is suitable of measuring the saturation of a material at a wicking height of 5 cm providing a measure of the partially saturated suction of such a material once in contact with Saline solution.

Figure 1:
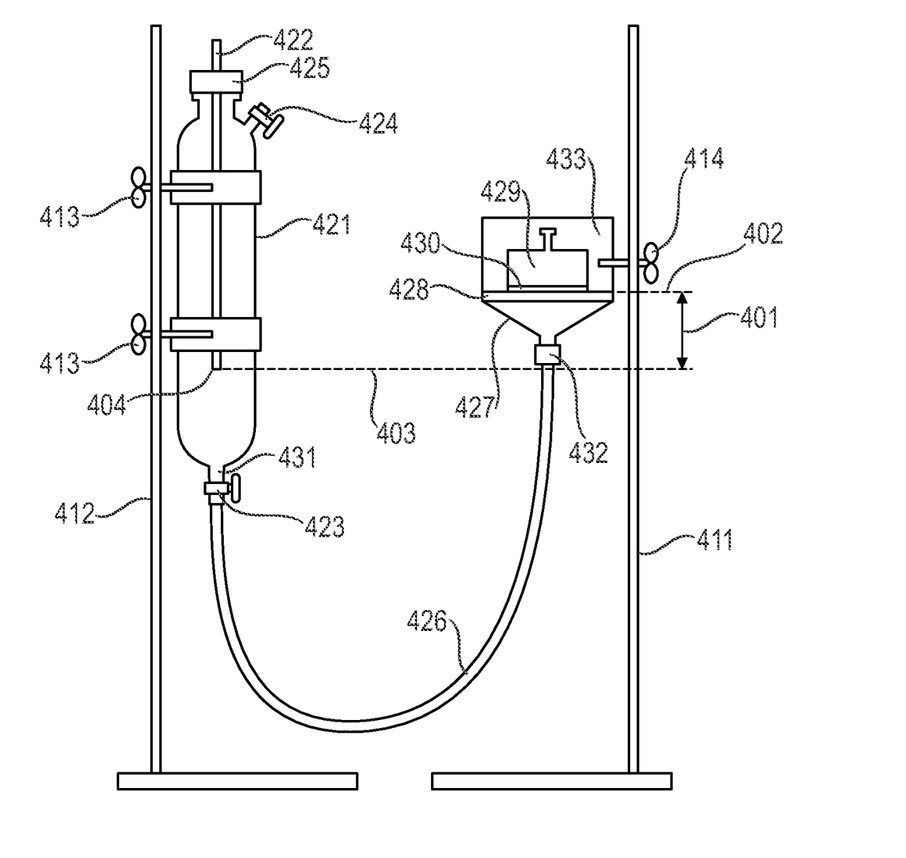
FIG. 1 is a side view of a Fixed Height Saturation (FHS) test apparatus.

General Apparatus Setup:

FIG. 1 shows the FHS measurements setup: a suitable fluid delivery reservoir 421, has an air tight stopcock 424 to allow the air release during the filling of the equipment. An open-ended glass tube 422 having an inner diameter of 10 mm extends through a port 425 in the top of the reservoir such that there is an airtight seal between the outside of the tube and the reservoir, this allows maintaining the required zero level of the hydro head during the experiment regardless the amount of liquid in the reservoir. Reservoir 421 is provided with delivery tube 431 having an inlet at the bottom of the reservoir, a stopcock 423, with the outlet connected to the bottom 432 of the sample holder funnel 427 via flexible plastic tubing 426 (e.g. Tygon®). The Fluid reservoir is firmly held in position by means of standard lab clamps 413 and a suitable lab support 412. The internal diameter of the delivery tube 431, stopcock 423, and flexible plastic tubing 426 enables fluid delivery to the sample holder funnel 427 at a high enough flow rate to completely wet the material in less than 30 seconds. The reservoir 421 has a capacity of approximately 1 liter. Other fluid delivery systems may be employed provided that they are able to deliver the fluid to the sample holder funnel 427 maintaining the zero level of the hydrostatic liquid pressure 403 at a constant height during the whole experiment.

The sample holder funnel 427 has a bottom connector with an internal diameter of 10 mm, a measurement and a chamber 433 where a glass frit 428 is accommodated. The sample holder chamber has a suitable size to accommodate the sample 430 and the confining pressure weight 429. The frit is sealed to the wall of the chamber 433. The glass frit has pore of specific size of 16-40 µm (glass frit type P 40, as defined by ISO 4793) and a thickness of 7 mm.

The confining pressure weight 429 is a cylinder with a diameter identical to the sample size (6 cm) and a weight of 593.94 g so to apply exactly 2.06 kPa of confining pressure to the sample 430. The sample holder funnel 427 is precisely held in position using a suitable lab support 411 through a standard lab clamp 414. The clamp should allow an easy vertical positioning of the sample holder funnel 427 such that the top of the glass frit 428 can be positioned at a) the same height (+/−1 mm) of the bottom end 404 of the open ended glass tube 422 and b) exactly 5 cm (+/−1 mm) above the bottom end 404 of the open ended glass tube 422. Alternatively two separated clamps are positioned at the abovementioned setups a and b and the sample holder funnel is alternatively moved from one to the other. During the non usage time, the instrument is kept in proper operating conditions flooding the sample holder funnel 427 with an excess of liquid to guarantee a proper wetting of the glass frit 428 that should be completely below the liquid level. The sample holder funnel 427 is also covered with an air tight cap (not shown) to avoid evaporation and therefore a change in solution salinity. During storage stopcocks 423 and 424 are also accordingly closed to avoid evaporation as well as the open ended tube 422 air tight sealed with a cap (not shown).

Sample Preparation

A disc of 6 cm diameter is prepared according to the above general procedure, the sample should be prepared out of the whole distribution material (e.g. a plurality of wet laid layers or folds).

Material Used:

Saline solution at a concentration of 0.9% by weight

FHS equipment

Bubble level analytical balance with a resolution of ±0.001 g with air draft protections.

Funnel

Tweezers

Timer

Experiment Setup

Before starting the experiment:

1) the caps to the open ended tube 422 and the sample holder funnel 427 are removed.
2) Ensuring the stopcock 423 is closed, the stopcock 424 is opened to allow the air to flow out of the liquid reservoir as displaced by liquid during the refilling phase. The liquid reservoir 421 is refilled through top end of the open-end tube 422 with the 0.9% Saline solution with the help of suitable means such a funnel (not shown) at the end of the filling the stopcock 424 is closed.

If during all the experiments the liquid level would be close to the bottom 404 of the open-ended tube 422, before running the next sample, the liquid reservoir must be refilled repeating this step number 2.

3) The sample holder funnel 427 is removed from the lab clamp 414 and the excess of liquid is removed pouring it away.
4) Manually holding the sample holder funnel 427 such that the top of the glass frit 428 lies around 10 cm below the bottom end 404 of the open-ended tube 422 the stop cock 423 is carefully open until the air liquid interface in the open ended tube 422 reaches the bottom end 404 and a few bubble of air escape from tube 422. At this point the stop cock 423 is closed.
5) The excess of liquid now present in the sample holder funnel 427 is again disposed and the system is now ready to start the measurements.

For each replicate:

1) The sample holder is positioned on the clamp 414 such that the top of the glass frit 428 lies exactly 5 cm (+/−1 mm) above the bottom end 404 of the open-ended tube 422. To ensure a reliable measure it is checked that the glass frit 428 is perfectly horizontal with the help of a bubble level.
2) Any remaining droplet of liquid on top of the glass frit are carefully removed by means of a filter paper of any other suitable material.
3) The sample is weighed with an analytical balance with a resolution of ±0.001 g. The Weight is recorded as Dry Sample Weight ($W_D$) to the nearest 0.001 g when the readings on the balance become constant.
4) The sample 430 is positioned in the center of the sample holder with the help of tweezers with particular care in not altering the orientation and relative position of each of the layers of the acquisition system. It is important that the topsheet facing side of each layer is facing now downwards during the experiment in the direction of the glass frit 428, reproducing the liquid flow entrance direction correctly.
5) The confining weight 429 is positioned centered on the sample
6) The stopcock 423 is opened for 30+/−1 seconds allowing liquid to flow in the sample and then closed again.
7) The confining weight 429 and the sample 430 are carefully removed from the glass frit 428 with the help of tweezers, it is important to keep track of the orientation of the sample and the relative position of the layers during the subsequent phases.
8) The sample 430 is weighed with the analytical balance with a resolution of ±0.001 g. The Weight is recorded as 5 cm Sample Weight ($W_5$) to the nearest 0.001 g when the readings on the balance become constant.
9) The sample 430 is positioned back on the frit with the confining weight 429 centered on top and the correct orientation and relative position of the layers.
10) The clamp 414 is moved (or the sample holder funnel 427 is positioned in another clamp) such that the top of the glass frit 428 lies exactly at the same height (+/−1 mm) of the bottom end 404 of the open-ended tube 422. To ensure a reliable measure it is checked that the glass frit 428 is perfectly horizontal with the help of a bubble level.
11) The stopcock 423 is opened again for 30+/−1 seconds allowing liquid to flow in the sample and then closed again.
12) The confining weight 429 and the sample 430 are carefully removed from the glass frit 428 with the help of tweezers
13) The sample 430 is weighted with the analytical balance with a resolution of ±0.001 g. The Weight is recorded as 0 cm Sample Weight ($W_0$) to the nearest 0.001 g when the readings on the balance become constant.

The measurements of a sample is now completed and a subsequent replicate can be measured repeating the above steps. Once terminated the series of experiment around 1 cm of liquid is added on the Sample Holder funnel 427 to completely submerge the glass frit 428. All the stopcock are closed and the cap positioned according to the storage condition explained above to avoid evaporation and ensure reliability of the subsequent measurements.

Calculations.

The FHS at 5 cm ($FHS_5$) is defined according to the following formula, $$FHS_5 = \frac{W_5 - W_D}{W_0 - W_D} \cdot 100$$

$FHS_5$ is rounded to the nearest 0.1 and expressed as percentage.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A layered absorbent element for use in a disposable absorbent article, said layered absorbent element comprising:

i) a top layer having a first surface and a second surface, said top layer being a fibrous nonwoven layer having a basis weight of from about 20 gsm to about 100 gsm, and a thickness from about 0.25 mm to about 5 mm, said nonwoven layer being formed with first fibers having an average length from about 26 mm to about 200 mm,
said nonwoven layer having a fixed height saturation at about 5 cm above 40%; and
ii) a bottom layer having a first surface and a second surface, said first surface of said bottom layer being in direct contact with said second surface of said top layer, said bottom layer comprising superabsorbent polymer (SAP) and second fibers, wherein said second fibers comprise cellulosic fibers;
wherein a plurality of said second fibers protrude from said first surface of said bottom layer and penetrate into said top layer through its second surface;
wherein said nonwoven layer comprises from about 5% to about 70%, by weight of said nonwoven layer, of first multicomponent binder fibers and is thermally bonded by said first multicomponent binder fibers, and wherein said bottom layer comprises from about 2% to about 20%, by weight of said bottom layer, of second multicomponent binder fibers and is thermally bonded by said second multicomponent binder fibers; and
wherein said first multicomponent binder fibers are thermally bonded to at least some of said plurality of said second fibers protruding from said first surface of said bottom layer and penetrating into said top layer, wherein said first multicomponent binder fibers comprise about 1.0% $TiO_2$, and wherein at least some of said second multicomponent binder fibers protrude from said first surface of said bottom layer into said top layer and said second multicomponent binder fibers are thermally bonded to said first fibers; and said layered absorbent element is a unitary absorbent element and said bottom layer comprises at least a first sub-layer and a second sub-layer, said first sub-layer comprising a different composition than said second sub-layer said first sub-layer defines said first surface of said bottom layer and wherein said SAP is located only in said first sub-layer.

2. A layered absorbent element according to claim 1 wherein said layered absorbent element consists of said top layer and said bottom layer.

3. A layered absorbent element according to claim 1 wherein said first fibers have an average size of about 0.5 dtex to about 15 dtex.

4. A layered absorbent element according to claim 1 wherein said nonwoven layer is selected from the group consisting of needlepunched, hydroentangled, air through bonded, spunbonded, carded resin bonded, and melt blown nonwoven materials.

5. A layered absorbent element according to claim 1 wherein said nonwoven layer is selected from the group consisting of needlepunched and hydroentangled nonwoven materials.

6. A layered absorbent element according to claim 1 wherein said top layer comprises about 10% to about 60%, by weight of said top layer, of said first multicomponent binder fibers.

7. A layered absorbent element according to claim 1 wherein said nonwoven layer is a hydroentangled fibrous structure having a basis weight from about 35 gsm to about 65 gsm, a machine direction bending stiffness of about 0.2 mN·cm to about 7 mN·cm, and a rewet value of about 0.2 g to about 7.0 g, and comprises about 30% to about 60%, by weight of said nonwoven layer, of cellulosic fibers, about 5% to about 30%, by weight of said nonwoven layer, of non-cellulosic fibers, and about 30% to about 55%, by weight of said nonwoven layer, of polyolefin-based multicomponent binder fibers.

8. A layered absorbent element according to claim 1 wherein said bottom layer is selected from the group consisting of an air laid material and a wet laid material.

9. A layered absorbent element according to claim 1 wherein no adhesive binders are present at an interface between said top layer and said bottom layer.

10. A disposable absorbent article comprising a layered absorbent element according to claim 1.

11. An absorbent article according to claim 10 wherein said article is selected from the group consisting of a diaper, a sanitary napkin, a pantyliner, an adult incontinence pad, and an adult incontinence diaper.

12. A layered absorbent element according to claim 1, wherein said first sub-layer defines said first surface of said bottom layer and wherein said second multicomponent fibers are located only in said first sub-layer.

13. A layered absorbent element according to claim 1, wherein said layered absorbent element is a unitary absorbent element, said bottom layer comprising a first outermost sub-layer defining said first surface of said bottom layer, a second outermost sub-layer, and at least one inner sub-layer located between said first and second outermost sub-layers, wherein said SAP is located only in said at least one inner sub-layer.

\* \* \* \* \*